United States Patent [19]

Nyffeler et al.

[11] Patent Number: 4,911,751

[45] Date of Patent: Mar. 27, 1990

[54] PROCESS FOR SELECTIVELY CONTROLLING WEEDS IN CROPS OF USEFUL PLANTS

[75] Inventors: Andreas Nyffeler, Magden, Switzerland; Reinhold Stauss, Freiburg, Fed. Rep. of Germany

[73] Assignee: Ciba-Geigy Corporation, Ardsley, N.Y.

[21] Appl. No.: 908,911

[22] Filed: Sep. 18, 1986

Related U.S. Application Data

[63] Continuation of Ser. No. 719,594, Apr. 3, 1985, abandoned.

[30] Foreign Application Priority Data

Apr. 11, 1984 [CH] Switzerland .......................... 1821/84

[51] Int. Cl.$^4$ .............................................. A01N 43/66
[52] U.S. Cl. .............................................. 71/93; 71/90; 71/92; 47/57.6
[58] Field of Search ................... 71/92, 93, 90; 47/57.6

[56] References Cited

U.S. PATENT DOCUMENTS

| | | | |
|---|---|---|---|
| 3,855,219 | 12/1974 | Fuchs et al. | 71/93 |
| 3,989,501 | 11/1976 | Kuratle, III | 71/77 |
| 4,127,405 | 11/1978 | Levitt | 71/93 |
| 4,272,920 | 6/1981 | Dawson . | |
| 4,394,506 | 7/1983 | Levill | 544/321 |
| 4,545,811 | 10/1985 | Meyer et al. | 71/93 |

FOREIGN PATENT DOCUMENTS

| | | |
|---|---|---|
| 4163 | 9/1979 | European Pat. Off. . |
| 7687 | 2/1980 | European Pat. Off. . |
| 13480 | 7/1980 | European Pat. Off. . |
| 23141 | 1/1981 | European Pat. Off. . |
| 23422 | 2/1981 | European Pat. Off. . |
| 30139 | 6/1981 | European Pat. Off. . |
| 30142 | 6/1981 | European Pat. Off. . |
| 35893 | 9/1981 | European Pat. Off. . |
| 44211 | 1/1982 | European Pat. Off. . |
| 44212 | 1/1982 | European Pat. Off. . |
| 44213 | 1/1982 | European Pat. Off. . |
| 44807 | 1/1982 | European Pat. Off. . |
| 44808 | 1/1982 | European Pat. Off. . |
| 44809 | 1/1982 | European Pat. Off. . |
| 51466 | 5/1982 | European Pat. Off. . |
| 57546 | 8/1982 | European Pat. Off. . |
| 70802 | 1/1983 | European Pat. Off. . |
| 72347 | 2/1983 | European Pat. Off. . |
| 73562 | 3/1983 | European Pat. Off. . |
| 79683 | 5/1983 | European Pat. Off. . |
| 83975 | 7/1983 | European Pat. Off. . |
| 84020 | 7/1983 | European Pat. Off. . |
| 84224 | 7/1983 | European Pat. Off. . |
| 85028 | 8/1983 | European Pat. Off. . |
| 85476 | 8/1983 | European Pat. Off. . |
| 87780 | 9/1983 | European Pat. Off. . |
| 95925 | 12/1983 | European Pat. Off. . |
| 96002 | 12/1983 | European Pat. Off. . |
| 96593 | 12/1983 | European Pat. Off. . |
| 99339 | 1/1984 | European Pat. Off. . |
| 102925 | 3/1984 | European Pat. Off. . |
| 107979 | 5/1984 | European Pat. Off. . |
| 117014 | 6/1984 | European Pat. Off. . |

OTHER PUBLICATIONS

Dale, Weed Research, vol. 23 (1983) pp. 63–68.
J. H. Dawson, Weed Science, 1983, vol. 31, 103–108.

*Primary Examiner*—Catherine L. Mills
*Attorney, Agent, or Firm*—Kevin T. Mansfield; Edward McC. Roberts

[57] ABSTRACT

A novel process for selectively controlling weeds in crops of useful plants in the pre-emergence process by the use of herbicidal sulfonylurea derivatives, which process comprises applying the herbicidal active substance in close proximity to and simultaneously with the cultivated-plant seed to the cultivated area.

13 Claims, No Drawings

PROCESS FOR SELECTIVELY CONTROLLING WEEDS IN CROPS OF USEFUL PLANTS

This application is a continuation of application Ser. No. 719,594, filed Apr. 3, 1985, abandoned.

The present invention relates to a novel process for selectively controlling weeds in crops of useful plants in the pre-emergence process.

According to conventional agricultural practice, herbicides are applied in the pre- and post-emergence processes by treatment of the whole cultivated area. For the controlling or prevention of damage in crops of useful plants caused by fungus or insect infestation, there have been employed for a considerable time application methods more favorable with regard to cost, such as seed dressing or application of the fungicide or insecticide into the seed furrow. Such application methods for herbicides have hitherto become known only for relatively readily volatile herbicides, for example 5-ethyl-dipropyl-thiocarbamate (EPTC), from the U.S. Patent Specification No. 4,272,920, and Dale, Weed Research 23, 63–68 (1983), in lucerne, soya-bean or cotton crops.

The transferring of this application principle to other commercial herbicides, such as 5-(2,4-dichlorophenoxy)-2-nitrobenzoic acid methyl ester (Bifenox), 3-(3-chloro-4-methylphenyl)-1,1-dimethylurea (Chlortoluron) or N-(1-ethylpropyl)-3,4-dimethyl-2,6-dinitroaniline (N-(1-ethylpropyl)-2,6-dinitro-3,4-xylidene), in the case of other cultivated crops, such as cereals, is not possible. Corresponding tests show damage to the cultivated plants without noticeable impairment of the weed population. This different action of EPTC and of other herbicides (Bifenox, Chlortoluron or N-(1-ethylpropyl)-2,6-dinitro-3,4-xylidene) is probably attributable to the good diffusion of EPTC in the form of a vapour in the soil, a property which these other herbicides do not have (cf. Weed Science 1983, Vol. 31, 103–108).

It has now been found that, surprisingly, also difficultly volatile herbicides, such as herbicides from the sulfonylurea class, are suitable for seed treatment and for seed-furrow application for the purpose of the selective control of weeds in crops of cultivated plants.

There is therefore suggested according to the present invention a process for selectively controlling weeds in crops of cultivated plants, which process comprises applying the seed of the cultivated plants simultaneously with, and in close proximity to, a herbicidal sulfonylurea derivative to the cultivated area.

By application in close proximity is meant within the scope of the invention both the soil application of the herbicidal sulfonylurea into the seed furrow, or on a narrowly restricted area around the seed, and the sowing of the seed pretreated with the herbicide. The herbicidal active substance can be adhering to the surface of the seeds or can have penetrated into the surface.

Seed dressing has proved to be a particularly suitable method for pretreating seed. Seed dressing with fungicidal or insecticidal active substances is a known process generally applied in modern agricultural practice. The herbicidal sulfonylurea derivatives which are to be used can be added in solid or liquid formulations to the seed in a commercial dressing apparatus. The seed-dressing operation is considered finished when the intended amount of active substance has been uniformly distributed over the seed(s).

The process according to the invention offers, besides a saving in field-working operations, also a saving in the amount of herbicides used, in consequence of which there are simultaneously obtained a cost reduction for the person applying the herbicides and a lower level of contamination of the environment with pesticides. Thus, the seed and the herbicidal sulfonylurea derivatives to be used can be applied to the field in a single operation. By virtue of the particular form of herbicidal application, only the weeds in the immediate vicinity of the cultivated plants are specifically controlled, so that the herbicide no longer has to be present in an active concentration over the entire cultivated area, as a result of which there is also a saving in the amount of herbicide used.

There are preferably employed, either by application of the herbicidal sulfonylurea into the seed furrow or by treatment of the seed(s) before sowing, amounts of 0.001 kg to 1 kg of active substance per hectare. Depending on the seed density, there are used in seed dressing, per kilogram of seed, formulated herbicides in amounts which correspond to amounts of active ingredient of between 0.01 g and 100.00 g. The amount of active ingredient is preferably regulated according to the degree of weed control desired. With respect to the cultivated plants, the applied dosage of herbicide is not critical and can vary within a wide range. In some crops it can be quite an advantage when the weeds are not completely removed and can thus counteract soil erosion. The amount of herbicide in this case is selected to ensure that the competitive strength of the weeds (especially in the close vicinity of the cultivated plants) is weakened only in the early development stages of the cultivated plants when they are sensitive to competition from weeds.

The herbicidal sulfonylureas used in the process according to the invention are applied in general in the form of commercial preparations. There may be given by way of example the following formulations for active ingredients of the sulfonylurea class:

FORMULATION EXAMPLES (%=PERCENT BY WEIGHT)

| (a) Dispersible powders | (a) | (b) | (c) | (d) | (e) |
| --- | --- | --- | --- | --- | --- |
| active ingredient | 20% | 60% | 0.5% | 0.1% | 90% |
| Na lignin sulfonate | 5% | 5% | 5% | 5% | 5% |
| Na laurylsulfate | 3% | — | — | — | 3% |
| Na diisobutyl-naphthalene sulfonate | — | 6% | 6% | 6% | — |
| octylphenolpolyethylene glycol ether (7–8 mols of ethylene oxide) | — | 2% | 2% | 2% | — |
| highly dispersed silicic acid | 5% | 27% | 27% | 27% | 2% |
| kaolin | 67% | — | — | — | — |
| sodium chloride | — | — | 59.5% | 59.9% | — |

The active ingredient is well mixed with the additives and the mixture is thorougly ground in a suitable mill.

| (b) Solution concentrate | (a) | (b) | (c) | | | |
| --- | --- | --- | --- | --- | --- | --- |
| active ingredient | 1% | 5% | 10% | | | |
| methylene chloride | 99% | 95% | 90% | | | |
| (c) Dusts | (a) | (b) | (c) | (d) | (e) | (f) | (g) |
| active ingredient | 0.1% | 1% | 10% | 20% | 10% | 10% | 80% |

-continued

| | | | | | | | |
|---|---|---|---|---|---|---|---|
| talcum | 99.9% | — | 90% | 80% | — | 45% | 20% |
| kaolin | — | 99% | — | — | — | — | — |
| active charcoal | — | — | — | — | 90% | 45% | — |

Dusts ready for use are obtained by mixing the active ingredient with the carriers, and grinding the mixture in a suitable mill.

| (d) Suspension concentrate | (a) | (b) |
|---|---|---|
| active ingredient | 40% | 5% |
| ethylene glycol | 10% | 10% |
| nonylphenol polyethylene glycol ether (15 mols of ethylene oxide) | 6% | 1% |
| Na lignin sulfonate | 10% | 5% |
| carboxymethyl cellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives.

| (e) Salt solution | |
|---|---|
| active ingredient | 5% |
| isopropylamine | 1% |
| octylphenolpolyethylene glycol ether | 3% |
| water | 91% |
| (f) Salt solution | |
| sodium salt of an active ingredient | 5% |
| octylphenolpolyethylene glycol ether | 3% |
| water | 92% |

Herbicidal sulfonylureas to be used according to the invention have been described in considerable numbers in the literature, and are in part already available commercially. Preferred active substances which are used in the process according to the present invention are described for example in the following publications: U.S. Patent Specification No. 4,127,405; European Patent Applications Nos.: EP-A 4,163, EP-A 4,687, EP-A 13,480, EP-A 23,141, EP-A 23,422, EP-A 30,139, EP-A 30,142, EP-A 35,893, EP-A 44,211, EP-A 44,212, EP-A 44,213, EP-A 44,807, EP-A 44,808, EP-A 44,809, EP-A 48,143, EP-A 51,466, EP-A 57,546, EP-A 70,802, EP-A 72,347, EP-A 73,652, EP-A 79,683, EP-A 83,975, EP-A 84,020, EP-A 84,224, EP-A 85,028, EP-A 85,476, EP-A 87,780, EP-A 95,925, EP-A 96,002, EP-A 96,593, EP-A 99,339, EP-A 102,925, EP-A 107,979 and EP-A 117,014.

Particularly preferred amongst this large group of active substances are those which are described by the general formula I

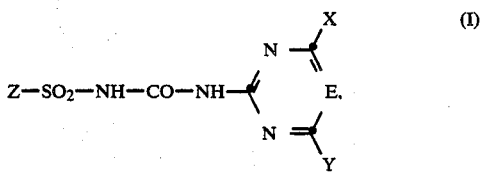

or salts thereof, wherein
Z is a radical

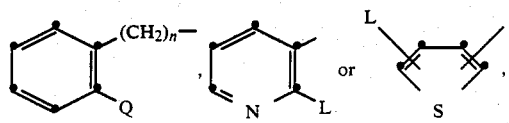

L is halogen, nitron, $-SO_2N(CH_3)_2$, $C_1-C_5$-alkoxycarbonyl, $C_1-C_5$-alkyl, $C_1-C_5$-alkoxy, $C_1-C_5$-alkylthio or $C_1-C_5$-alkylsulfonyl, Q is halogen, nitro, $-SO_2N(CH_3)_2$, $-CO-R^1$, $-(A)_m-R^2$, phenyl, phenoxy, $C_1-C_5$-alkyl, halophenyl, halophenoxy, $C_1-C_5$-haloalkoxy, $C_1-C_5$-haloalkylthio or $C_1-C_5$-haloalkyl, n is the number zero or one, E is nitrogen or the methine bridge, X is methyl, methoxy or cyclopropyl, and Y is chlorine, methoxy, difluoromethoxy or ethoxy, where $R^1$ is hydrogen, $C_1-C_5$-alkyl, $C_1-C_5$-alkoxy, $C_3-C_5$-alkenyloxy or $C_3-C_5$-alkynyloxy, A is oxygen, sulfur, $-SO-$, $-SO_2-$ or $-O-SO_2-$, m is the number zero or one, and $R^2$ is $C_1-C_5$-alkyl, $C_2-C_5$-alkenyl, $C_2-C_5$-alkenyl, $C_1-C_5$-haloalkyl, $C_2-C_7$-alkoxyalkyl, $C_2-C_5$-haloalkenyl or $C_2-C_5$-haloalkynyl, with the proviso that $R^2$ cannot be $-CH=CH_2$ or $-C\equiv CH$ when m is the number one.

The active substances of the formula I are advantageously applied in crops of cereals, rice, soya-bean, maize or rape-seed for the pre-emergence selective controlling of weeds in the process according to the present invention.

Suitable in a particular manner for use in cereal crops, especially in wheat and barley crops, are sulfonylureas of the narrower formula Ia

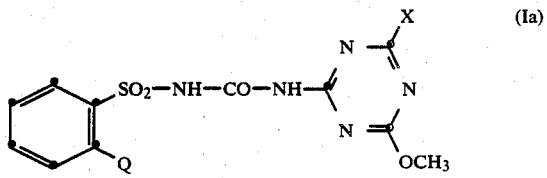

wherein

X is methyl or methoxy,

Q is halogen, $-SO_2N(CH_3)_2$, $-CO-R^1$ or $-(A)_m-R^2$, and $R^1$ is hydrogen, $C_1-C_5$-alkyl, $C_1-C_5$-alkoxy, $C_3-C_5$-alkenyloxy or $C_3-C_5$-alkynyloxy, A is oxygen, sulfur, $-SO-$, $-SO_2-$ or $-O-SO_2-$, m is the number zero or one, and $R^2$ is $C_1-C_5$-alkyl, $C_2-C_5$-alkenyl, $C_2-C_5$-alkynyl, $C_1-C_5$-haloalkyl, $C_2-C_7$-alkoxyalkyl, $C_2-C_5$-haloalkenyl or $C_2-C_5$-haloalkynyl, with the proviso that $R^2$ cannot be $-CH=CH_2$ or $-C\equiv CH$ when m is the number one.

To be emphasized among the compounds of the formula Ia are those in which the symbol Q is 2-chloroethoxy, 2-methoxyethoxy, chlorine or methoxycarbonyl. Preferred active substances are:

N-[2-(2-chloroethoxy)phenylsulfonyl]-N'-(4-methoxy-6-methyl-1,3,5-triazin-2-yl) urea, N-[2-(2-methoxyethoxy)phenylsulfonyl]-N'-(4-methoxy-6-methyl-1,3,5-triazin-2-yl) urea, N-[2-(2-methoxyethoxy)-phenylsulfonyl]-N'-(4,6-dimethoxy-1,3,5-triazin-2-yl) urea,
N-(2-chlorophenylsulfonyl)-N'-(4-methoxy-6-methyl-1,3,5-triazin-2-yl) urea, and
N-(2-methoxycarbonylphenylsulfonyl)-N'-(4-methoxy-6-methyl-1,3,5-triazin-2-yl) urea.

Suitable in a preferred manner for use in rice crops are sulfonylureas of the formula Ib or Ic

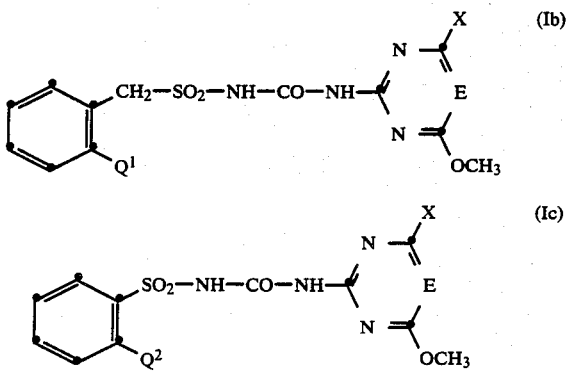

wherein
$Q^1$ is $C_1$–$C_4$-alkoxycarbonyl or $C_3$–$C_4$-alkenyloxycarbonyl,
$Q^2$ is phenyl, phenoxy, $C_1$–$C_5$-alkoxy, $C_1$–$C_5$-alkylthio, $C_1$–$C_5$-alkyl, halophenyl, halophenoxy, $C_1$–$C_5$-haloalkoxy, $C_1$–$C_5$-haloalkylthio, $C_1$–$C_5$-haloalkyl, $C_2$–$C_5$-alkoxyalkoxy, $C_2$–$C_5$-alkenyloxy or $C_2$–$C_5$-haloalkenyloxy,
E is nitrogen or the methine bridge, and
X is methyl or methoxy.

To be emphasised among the compounds of the formula Ib is that in which $Q^1$ is methoxycarbonyl, E is the methine bridge and X is methoxy, that is to say the compound N-(2-methoxycarbonylbenzylsulfonyl)-N'-(4,6-dimethoxypyrimidin-2-yl) urea.

Among the compounds of the formula Ic to be emphasised are those in which $Q^2$ is perfluoroethoxy, E is nitrogen or the methine bridge and X is methoxy; or $Q^2$ is phenyl, E is the methine bridge or nitrogen and X is methyl; or $Q^2$ is 2-methoxyethoxy, E is nitrogen and X is methoxy; or $Q^2$ is 2-isopentenyloxy, E is nitrogen and X is methoxy; or $Q^2$ is 1,2-dichlorovinyloxy, E is nitrogen and X is methoxy; that is to say, the compounds:
N-(2-perfluoroethoxyphenylsulfonyl)-N'-(4,6-dimethoxy-1,3,5-triazin-2-yl) urea,
N-(2-phenylphenylsulfonyl)-N'-(4-methoxy-6-methylpyrimidin-2-yl) urea,
N-[2-(2-methoxyethoxy)phenylsulfonyl]-N'-(4,6-dimethoxy-1,3,5-triazin-2-yl) urea,
N-(2-phenylphenylsulfonyl)-N'-(4-methoxy-6-methyl-1,3,5-triazin-2-yl) urea,
N-[2-(2-isopentenyloxy)phenylsulfonyl]-N'-(4,6-dimethoxy-1,3,5-triazin-2-yl) urea,
N-[2-(1,2-dichlorovinyloxy)phenylsulfonyl]-N'-(4,6-dimethoxy-1,3,5-triazin-2-yl) urea, and
N-(2-perfluoroethoxyphenylsulfonyl)-N'-(4,6-dimethoxypyrimidin-2-yl) urea.

Suitable in a particular manner for use in rape-seed crops is the active substance:
N-(2-methoxycarbonylphenylsulfonyl)-N'-(4-ethoxy-6-cyclopropyl-1,3,5-triazin-2-yl) urea.

The carrying out of the process according to the invention is economically particularly advantageous since only one single operation is necessary for the sowing of the seed of the cultivated plants and for the pre-emergence control of the weeds. There can thus be applied, in a single field operation, the seed and the herbicidal sulfonylurea, either by using specially developed seed-drilling machines, which feed the herbicide directly with the untreated seeds into the seed furrow, or preferably by using customary methods for the sowing of seed pretreated with the herbicide.

With this method of application, the herbicidal sulfonylurea spreads around the cultivated-plant seed in the soil, and thus forms a weed-free zone surrounding the developing seedlings of the cultivated plants. Within this zone, the weed growth is either completely prevented by the action of the herbicide or is so suppressed that the weeds can in no way compete with the cultivated plants in their early stage of development. In the case of sowing into the seed furrows, the circular, weed-free zones can merge together and can hence form an inhibitory zone for weeds on both sides of the seed furrow. Where there is an irregular sowing of the cultivated area, there possibly occurs a weed infestation whre no seed has been applied. With an adequately dense sowing of the area, or with a sufficiently narrow distance between the seed furrows, however, a complete suppression of the weed growth can be obtained.

Under unfavourable climatic conditions, the attainable advantage can also have a ecologically advantageous effect in that a weed covering or residues of withered plants survive and thus prevent an erosion and a drying out of the soil; and in that the competitor plants are held back only in the closest proximity of the germinating cultivated plants. Low costs of working the soil are moreover possible because the application process according to the present invention is suitable also for no-tillage cultivation methods.

The Example which follws serves to further illustrate the present invention.

BIOLOGICAL EXAMPLE

Description of the test

In a glass flask of 100 ml capacity, 30 g of wheat seed and 23 g of barley seed, respectively, are dressed with a formulated herbicide by rotation and shaking of the flask. The dressing amounts are per 30 g of wheat or 23 g of barley: 16, 13, 8.1, 6.5, 4.07, 3.25, 1.95, 1.63, 0.98, 0.81 or 0.41 mg of active substance.

The dressed seeds are sown together with weed seeds in sandy loam soil in plastic tanks (25 cm long, 17 cm wide and 12 cm high). All the seeds are evenly worked into the soil to a depth of 5 cm. In each case there are sown per seed tray the same number of weed seeds and 18 wheat seeds (corresponding to 180 kg/ha of seed) and 14 barley seeds (corresponding to 150 kg/ha of seed), respectively, so that the applied amount of herbicide, depending on the dressing amount, is 100, 80, 50, 40, 25, 20, 12, 10, 6, 5 or 2.5 g per hectare. After being sown, the seed tanks are watered regularly and are kept in a greenhouse at a temperature of 22° to 25° C., with 50 to 70% relative humidity. 38 days after sowing, the action of the herbicide compared with the result in the case of the untreated control specimens is assessed on the basis of the observed phytotoxicity.

Results

The tests results give the phytotoxicity in percent compared with that on untreated control specimens.

Plant which has died or not germinated: 100% phytotoxicity; untreated control plant: 0% phytotoxicity.

(a) Herbicide used for dressing:
N-[2-(2-chloroethoxy)phenylsulfonyl]-N'-(4-methoxy-6-methyl-1,3,5-triazin-2-yl) urea, formulated as a 1% wettable powder.

TABLE a

| Test plant | Applied amount [g AS/ha]* | | | |
|---|---|---|---|---|
| | 80 | 40 | 20 | 10 |
| wheat | 30 | 10 | 0 | 0 |
| Avena fatua | 60 | 40 | 15 | 15 |
| Lolium perenne | 100 | 97 | 97 | 95 |
| Apera spica-venti | 100 | 100 | 100 | 95 |
| Stellaria media | 100 | 100 | 100 | 97 |
| Galium aparine | 100 | 95 | 90 | 85 |
| Chenopodium album | 90 | 90 | 70 | 60 |

*grams of active substance per hectare

TABLE b

| Test plant | Applied amount [g AS/ha] | | | |
|---|---|---|---|---|
| | 20 | 10 | 5 | 2.5 |
| wheat | 5 | 0 | 0 | 0 |
| Avena fatua | 10 | 10 | 0 | 0 |
| Lolium perenne | 80 | 80 | 50 | 20 |
| Stellaria media | 100 | 97 | 97 | 90 |
| Galium aparine | 90 | 80 | 70 | 5 |
| Chenopodium album | 90 | 70 | 60 | 20 |

TABLE c

| Test plant | Applied amount [g AS/ha] | | | |
|---|---|---|---|---|
| | 80 | 40 | 20 | 10 |
| barley | 35 | 20 | 0 | 0 |
| Avena fatua | 50 | 40 | 40 | 40 |
| Lolium perenne | 97 | 97 | 90 | 85 |
| Apera spica-venti | 100 | 100 | 100 | 97 |
| Stellaria media | 100 | 95 | 95 | 95 |
| Galium aparine | 90 | 85 | 80 | 70 |
| Chenopodium album | 90 | 90 | 80 | 80 |

TABLE d

| Test plant | Applied amount [g AS/ha] | | | |
|---|---|---|---|---|
| | 20 | 10 | 5 | 2.5 |
| barley | 0 | 0 | 0 | 0 |
| Avena fatua | 10 | 10 | 0 | 0 |
| Lolium perenne | 90 | 80 | 60 | 50 |
| Stellaria media | 100 | 100 | 97 | 97 |
| Galium aparine | 95 | 80 | 60 | 50 |
| Chenopodium album | 90 | 60 | 60 | 50 |

(b) Herbicides used for dressing in the form of 25% dispersible powders:
Compound A: N-(2-chlorophenylsulfonyl)-N'-(4-methoxy-6-methyl-1,3,5-triazin-2-yl) urea,
Compound B: N-(2-difluoromethoxyphenylsulfonyl)-N'-(4-methoxy-6-methyl-1,3,5-triazin-2-yl) urea,
Compound D: N-[2-(2-methoxyethoxy)phenylsulfonyl]-N'-(4-methoxy-6-methyl-1,3,5-triazin-2-yl) urea,
Compound E: N-[2-(2,2,2-trifluoroethoxy)phenylsulfonyl]-N'-(4-methoxy-6-methyl-1,3,5-triazin-2-yl) urea,
Compound F: N-(2-propyloxyphenylsulfonyl)-N'-(4,6-dimethoxy-1,3,5-triazin-2-yl) urea, and
Compound G: N-(2-propyloxyphenylsulfonyl)-N'-(4-methoxy-6-methyl-1,3,5-triazin-2-yl) urea.

TABLE e

Tested herbicide: compound A

| Test plant | Applied amount [g AS/ha] | | | | |
|---|---|---|---|---|---|
| | 100 | 50 | 25 | 12 | 6 |
| wheat | 80 | 50 | 10 | 0 | 0 |
| Lolium perenne | 95 | 85 | 80 | 50 | 20 |
| Stellaria media | 97 | 80 | 70 | 50 | 50 |
| Chenopodium album | 95 | 90 | 80 | 60 | 20 |
| Veronica persica | 97 | 90 | 90 | 70 | 30 |
| Galium aparine | 97 | 90 | 90 | 40 | 10 |

TABLE f

Tested herbicide: compound A

| Test plant | Applied amount [g AS/ha] | | | | |
|---|---|---|---|---|---|
| | 100 | 50 | 25 | 12 | 6 |
| barley | 40 | 30 | 5 | 0 | 0 |
| Lolium perenne | 95 | 95 | 90 | 50 | 40 |
| Stellaria media | 90 | 100 | 85 | 50 | 40 |
| Chenopodium album | 97 | 97 | 97 | 60 | 40 |
| Veronica persica | 95 | 95 | 95 | 70 | 40 |
| Galium aparine | 90 | 90 | 70 | 40 | 20 |

TABLE g

Tested herbicide: compound B

| Test plant | Applied amount [g AS/ha] | | | | |
|---|---|---|---|---|---|
| | 100 | 50 | 25 | 12 | 6 |
| wheat | 60 | 50 | 10 | 0 | 0 |
| Lolium perenne | 100 | 95 | 95 | 95 | 30 |
| Stellaria media | 100 | 100 | 100 | 100 | 50 |
| Chenopodium album | 100 | 100 | 97 | 97 | 50 |
| Veronica persica | 100 | 95 | 95 | 95 | 95 |
| Galium aparine | 60 | 50 | 40 | 40 | 10 |

TABLE h

Tested herbicide: compound B

| Test plant | Applied amount [g AS/ha] | | | | |
|---|---|---|---|---|---|
| | 100 | 50 | 25 | 12 | 6 |
| barley | 50 | 40 | 5 | 0 | 0 |
| Lolium perenne | 100 | 100 | 100 | 90 | 30 |
| Stellaria media | 100 | 100 | 100 | 80 | 50 |
| Chenopodium album | 100 | 100 | 100 | 95 | 70 |
| Veronica persica | 100 | 100 | 100 | 95 | 70 |
| Galium aparine | 50 | 60 | 60 | 20 | 10 |

TABLE i

Tested herbicide: compound C

| Test plant | Applied amount [g AS/ha] | | | | |
|---|---|---|---|---|---|
| | 100 | 50 | 25 | 12 | 6 |
| wheat | 10 | 0 | 0 | 0 | 0 |
| Lolium perenne | 90 | 70 | 30 | 0 | 0 |
| Stellaria media | 100 | 70 | 10 | 0 | 0 |
| Chenopodium album | 80 | 70 | 10 | 0 | 0 |
| Veronica persica | 95 | 95 | 10 | 0 | 0 |
| Galium aparine | 90 | 75 | 10 | 0 | 0 |

TABLE j

Tested herbicide: compound C

| Test plant | Applied amount [g AS/ha] | | | | |
|---|---|---|---|---|---|
| | 100 | 50 | 25 | 12 | 6 |
| barley | 30 | 20 | 10 | 0 | 0 |
| Lolium perenne | 9 | 90 | 50 | 50 | 10 |
| Stellaria media | 100 | 60 | 60 | 60 | 10 |
| Chenopodium album | 90 | 50 | 30 | 30 | 0 |
| Veronica persica | 100 | 50 | 50 | 50 | 0 |
| Galium aparine | 97 | 50 | 40 | 40 | 10 |

TABLE k

Tested herbicide: compound D

| Test plant | Applied amount [g AS/ha] | | | | |
|---|---|---|---|---|---|
| | 100 | 50 | 25 | 12 | 6 |
| wheat | 10 | 0 | 0 | 0 | 0 |
| Lolium perenne | 80 | 10 | 0 | 0 | 0 |
| Stellaria media | 95 | 30 | 10 | 0 | 0 |
| Chenopodium album | 95 | 40 | 30 | 0 | 0 |
| Veronica persica | 97 | 50 | 20 | 0 | 0 |
| Galium aparine | 70 | 10 | 0 | 0 | 0 |

TABLE l

Tested herbicide: compound D

| Test plant | Applied amount [g AS/ha] | | | | |
|---|---|---|---|---|---|
| | 100 | 50 | 25 | 12 | 6 |
| barley | 10 | 0 | 0 | 0 | 0 |
| Lolium perenne | 90 | 20 | 20 | 10 | 10 |
| Stellaria media | 80 | 30 | 30 | 0 | 0 |
| Chenopodium album | 80 | 40 | 20 | 0 | 0 |
| Veronica persica | 80 | 50 | 30 | 10 | 10 |
| Galium aparine | 80 | 30 | 20 | 0 | 0 |

TABLE m

Tested herbicide: compound E

| Test plant | Applied amount [g AS/ha] | | | | |
|---|---|---|---|---|---|
| | 100 | 50 | 25 | 12 | 6 |
| wheat | 20 | 15 | 0 | 0 | 0 |
| Lolium perenne | 97 | 95 | 90 | 80 | 10 |
| Stellaria media | 100 | 100 | 97 | 95 | 30 |
| Chenopodium album | 100 | 100 | 95 | 90 | 40 |
| Veronica persica | 100 | 100 | 95 | 90 | 40 |
| Galium aparine | 95 | 75 | 60 | 60 | 20 |

TABLE n

Tested herbicide: compound E

| Test plant | Applied amount [g AS/ha] | | | | |
|---|---|---|---|---|---|
| | 100 | 50 | 25 | 12 | 6 |
| barley | 40 | 10 | 0 | 0 | 0 |
| Lolium perenne | 97 | 97 | 95 | 90 | 50 |
| Stellaria media | 100 | 100 | 100 | 100 | 60 |
| Chenopodium album | 97 | 97 | 90 | 90 | 50 |
| Veronica persica | 100 | 100 | 100 | 100 | 50 |
| Galium aparine | 80 | 75 | 70 | 70 | 40 |

TABLE o

Tested herbicide: compound F

| Test plant | Applied amount [g AS/ha] | | | | |
|---|---|---|---|---|---|
| | 100 | 50 | 25 | 12 | 6 |
| wheat | 0 | 0 | 0 | 0 | 0 |
| Lolium perenne | 70 | 50 | 30 | 10 | 0 |
| Stellaria media | 90 | 70 | 70 | 30 | 30 |
| Chenopodium album | 90 | 90 | 90 | 60 | 60 |
| Veronica persica | 80 | 80 | 70 | 50 | 40 |
| Galium aparine | 90 | 60 | 40 | 10 | 10 |

TABLE p

Tested herbicide: compound F

| Test plant | Applied amount [g AS/ha] | | | | |
|---|---|---|---|---|---|
| | 100 | 50 | 25 | 12 | 6 |
| barley | 10 | 0 | 0 | 0 | 0 |
| Lolium perenne | 90 | 50 | 50 | 50 | 0 |
| Stellaria media | 100 | 70 | 50 | 50 | 30 |
| Chenopodium album | 100 | 80 | 75 | 75 | 50 |
| Veronica persica | 100 | 80 | 60 | 50 | 30 |
| Galium aparine | 90 | 50 | 50 | 50 | 10 |

TABLE q

Tested herbicide: compound G

| Test plant | Applied amount [g AS/ha] | | | | |
|---|---|---|---|---|---|
| | 100 | 50 | 25 | 12 | 6 |
| wheat | 20 | 15 | 10 | 0 | 0 |
| Lolium perenne | 97 | 90 | 90 | 50 | 50 |
| Stellaria media | 100 | 80 | 80 | 40 | 40 |
| Chenopodium album | 97 | 97 | 90 | 50 | 50 |
| Veronica persica | 100 | 97 | 97 | 60 | 60 |
| Galium aparine | 100 | 70 | 70 | 40 | 40 |

TABLE r

Tested herbicide: compound G

| Test plant | Applied amount [g AS/ha] | | | | |
|---|---|---|---|---|---|
| | 100 | 50 | 25 | 12 | 6 |
| barley | 60 | 40 | 0 | 0 | 0 |
| Lolium perenne | 80 | 80 | 90 | 75 | 20 |
| Stellaria media | 80 | 95 | 95 | 80 | 20 |
| Chenopodium album | 95 | 95 | 95 | 95 | 40 |
| Veronica persica | 95 | 95 | 95 | 95 | 40 |
| Galium aparine | 90 | 90 | 90 | 60 | 20 |

(c) Commercial herbicides used for dressing:

Compound X: 5-(2,4-dichlorophenoxy)-2-nitrobenzoic acid in the form of a 48% suspension concentrate;

Compound Y: 3-(3-chloro-4-methylbenzyl)-1,1-dimethylurea in the form of an 80% dispersible powder; and Compound Z: N-(1-ethylpropyl)-3,4-dimethyl-2,6-dinitroaniline in the form of a 34% emulsion concentrate.

In these tests, the applied amounts of active substance has to be considerably increased in order to obtain a plant-influencing effect. The applied amounts are 3200, 1600, 800, 400 and 200 g of active substance per hectare. The active substances do not belong to the herbicidal sulfonylurea class, but are customary commercial herbicides for use in cereal crops.

TABLE s

Tested herbicide: compound X

| Test plant | Applied amount [g AS/ha] | | | | |
|---|---|---|---|---|---|
| | 3200 | 1600 | 800 | 400 | 200 |
| wheat | 10 | 0 | 0 | 0 | 0 |
| Lolium perenne | 0 | 0 | 0 | 0 | 0 |
| Stellaria media | 0 | 0 | 0 | 0 | 0 |
| Chenopodium album | 0 | 0 | 0 | 0 | 0 |
| Veronica persica | 0 | 0 | 0 | 0 | 0 |
| Galium aparine | 0 | 0 | 0 | 0 | 0 |

TABLE t

Tested herbicide: compound X

| Test plant | Applied amount [g AS/ha] | | | | |
|---|---|---|---|---|---|
| | 3200 | 1600 | 800 | 400 | 200 |
| barley | 0 | 0 | 0 | 0 | 0 |
| Lolium perenne | 0 | 0 | 0 | 0 | 0 |
| Stellaria media | 0 | 0 | 0 | 0 | 0 |
| Chenopodium album | 0 | 0 | 0 | 0 | 0 |
| Veronica persica | 0 | 0 | 0 | 0 | 0 |
| Galium aparine | 0 | 0 | 0 | 0 | 0 |

TABLE u

Tested herbicide: compound Y

| Test plant | Applied amount [g AS/ha] | | | | |
|---|---|---|---|---|---|
| | 3200 | 1600 | 800 | 400 | 200 |
| wheat | 100 | 100 | 100 | 100 | 50 |
| Lolium perenne | 50 | 30 | 0 | 0 | 0 |
| Stellaria media | 40 | 0 | 0 | 0 | 0 |

TABLE u-continued

Tested herbicide: compound Y

| Test plant | Applied amount [g AS/ha] | | | | |
|---|---|---|---|---|---|
| | 3200 | 1600 | 800 | 400 | 200 |
| Chenopodium album | 50 | 10 | 0 | 0 | 0 |
| Veronica persica | 30 | 0 | 0 | 0 | 0 |
| Galium aparine | 0 | 0 | 0 | 0 | 0 |

TABLE v

Tested herbicide: compound Y

| Test plant | Applied amount [g AS/ha] | | | | |
|---|---|---|---|---|---|
| | 3200 | 1600 | 800 | 400 | 200 |
| barley | 100 | 100 | 100 | 100 | 50 |
| Lolium perenne | 40 | 20 | 0 | 0 | 0 |
| Stellaria media | 0 | 0 | 0 | 0 | 0 |
| Chenopodium album | 30 | 0 | 0 | 0 | 0 |
| Veronica persica | 0 | 0 | 0 | 0 | 0 |
| Galium aparine | 0 | 0 | 0 | 0 | 0 |

TABLE w

Tested herbicide: compound Z

| Test plant | Applied amount [g AS/ha] | | | | |
|---|---|---|---|---|---|
| | 3200 | 1600 | 800 | 400 | 200 |
| wheat | 100 | 100 | 100 | 100 | 50 |
| Lolium perenne | 0 | 0 | 0 | 0 | 0 |
| Stellaria media | 0 | 0 | 0 | 0 | 0 |
| Chenopodium album | 0 | 0 | 0 | 0 | 0 |
| Veronica persica | 0 | 0 | 0 | 0 | 0 |
| Galium aparine | 0 | 0 | 0 | 0 | 0 |

TABLE x

Tested herbicide: compound Z

| Test plant | Applied amount [g AS/ha] | | | | |
|---|---|---|---|---|---|
| | 3200 | 1600 | 800 | 400 | 200 |
| barley | 100 | 100 | 100 | 100 | 100 |
| Lolium perenne | 0 | 0 | 0 | 0 | 0 |
| Stellaria media | 0 | 0 | 0 | 0 | 0 |
| Chenopodium album | 0 | 0 | 0 | 0 | 0 |
| Veronica persica | 0 | 0 | 0 | 0 | 0 |
| Galium aparine | 0 | 0 | 0 | 0 | 0 |

What is claimed is:

1. A process for selectively controlling weeds in crops of useful plants preemergence, which process comprises applying a herbicidal sulfonylurea of the formula

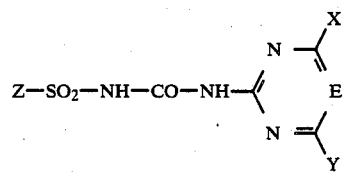

or a salt thereof, in which formula
Z is a radical

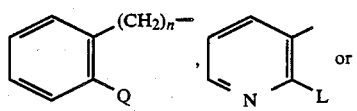

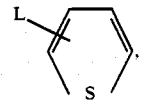

L is halogen, nitro, —SO$_2$N(CH$_3$)$_2$, C$_1$–C$_5$-alkoxycarbonyl, C$_1$–C$_5$-alkyl, C$_1$–C$_5$-alkoxy, C$_1$–C$_5$-alkylthio or C$_1$–C$_5$-alkylsulfonyl, Q is halogen, nitro, —SO$_2$N(CH$_3$)$_2$, —CO—R$^1$, —(A)$_m$—R$^2$, phenyl, phenoxy, C$_1$–C$_5$-alkyl, halophenyl, halophenoxy, C$_1$–C$_5$-haloalkoxy, C$_1$–C$_5$-haloalkylthio or C$_1$–C$_5$-haloalkyl, n is the number zero or one, E is nitrogen or the methine bridge, X is methyl, methoxy or cyclopropyl, and Y is chlorine, methoxy, difluoromethoxy or ethoxy, where R$^1$ is hydrogen, C$_1$–C$_5$-alkyl, C$_1$–C$_5$-alkoxy, C$_3$–C$_5$-alkenyloxy or C$_3$–C$_5$-alkynyloxy, A is oxygen, sulfur, —SO—, —SO$_2$— or —O—SO$_2$—, m is the number zero or one, and R is C$_1$–C$_5$-alkyl, C$_2$–C$_5$-alkenyl, C$_2$–C$_5$-alkynyl, C$_1$–C$_5$-haloalkyl, C$_2$–C$_7$-alkoxyalkyl, C$_2$–C$_5$-haloalkenyl or C$_2$–C$_5$-haloalkynyl, with the proviso that R$^2$ cannot be —CH=CH$_2$ or —C≡CH when m is the number one, nonuniformly to the area to be cultivated, either by sowing seeds of said cultivated plants which have been pretreated with a herbicidally effective amount of said herbicide, or by applying a herbicidally effective amount of said herbicide simultaneously with untreated seed only into the seed furrow or seed hole.

2. A process of claim 1, wherein the seed has been treated with the herbicidal sulfonylurea.

3. A process of claim 2, wherein the seed has been dressed with the herbicidal sulfonylurea.

4. A process of claim 1, wherein the seed and the herbicidal sulfonylurea are applied in the same seed furrow.

5. A process of claim 1, wherein between 0.001 kg and 1 kg of sulfonylurea is applied per hectare of cultivated area.

6. A process of claim 2, wherein between 0.01 g and 100.00 g of sulfonylurea are used per kilogram of seed.

7. A process of claim 1, wherein the usefulplant seed is that of cereals, rice, soya-bean, maize or rape-seed.

8. A process of claim 1, wherein the seed is cereal seed and the sulfonylurea is a compound of the formula Ia

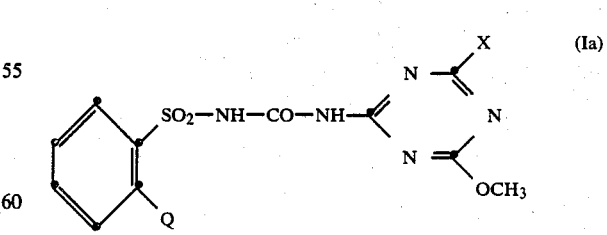

wherein
X is methyl or methoxy,
Q is halogen, —SO$_2$N(CH$_3$)$_2$, —CO—R$^1$ or —(A)-$_m$—R$^2$, and
R$^1$ is hydrogen, C$_1$–C$_5$-alkyl, C$_1$–C$_5$-alkoxy, C$_3$–C$_5$-alkenyloxy or C$_3$–C$_5$-alkynyloxy, A is oxygen, sulfur, —SO—, —SO$_2$— or —O—SO$_2$, m is the number zero or one, and R$_2$ is C$_1$–C$_5$-alkyl, C$_2$–C$_5$-alkenyl, C$_2$–C$_5$-alkynyl, C$_1$–C$_5$-haloalkyl, C$_2$–C$_7$-alkoxyalkyl, C$_2$–C$_5$-haloalkenyl or C$_2$–C$_5$-haloalkynyl, with the proviso that R$^2$ cannot be —CH=CH$_2$ or —C≡CH when m is the number one.

9. A process of claim 8, wherein in the sulfonylurea of the formula Ia the symbol Q is 2-chloroethoxy, 2-methoxyethoxy, chlorine or methoxycarbonyl.

10. A process of claim 1, wherein the seed is rice seed and the sulfonylurea is a compound of the formula Ib or Ic

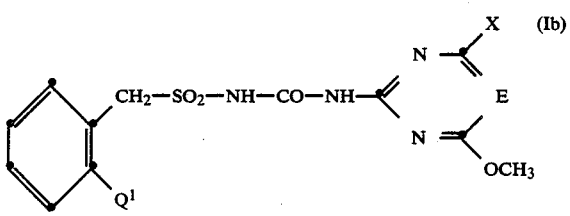

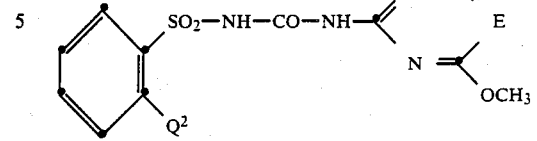

wherein
Q$^1$ is C$_1$–C$_4$-alkoxycarbonyl or C$_3$–C$_4$-alkenyloxycarbonyl,

Q$^2$ is phenyl, phenoxy, C$_1$–C$_5$-alkoxy, C$_1$–C$_5$-alkylthio, C$_1$–C$_5$-alkyl, halophenyl, halophenoxy, C$_1$–C$_5$-haloalkoxy, C$_1$–C$_5$-haloalkylthio, C$_1$–C$_5$-haloalkyl, C$_2$–C$_5$-alkoxyalkoxy, C$_2$–C$_5$-alkenyloxy or C$_2$–C$_5$-haloalkenyloxy, E is nitrogen or the methine bridge, and
X is methyl or methoxy.

11. A process of claim 10, wherein in the sulfonylurea of the formula Ib the symbol Q$^1$ is methoxycarbonyl, E is the methine bridge and X is methoxy.

12. A process of claim 10, wherein in the sulfonylurea of the formula Ic the symbol Q$^2$ is perfloroethoxy, E is nitrogen or the methine bridge and X is methoxy; or Q$^2$ is phenyl, E is the methine bridge or nitrogen and X is methyl; or Q$^2$ is 2-methoxyethoxy, E is nitrogen and X is methoxy; or Q$^2$ is 2-isopentenyloxy, E is nitrogen and X is methoxy; or Q$^2$ is 1,2-dichlorovinyloxy, E is nitrogen and X is methoxy.

13. A process of claim 1, wherein the seed is rapeseed and the sulfonylurea is N-(2-methoxycarbonylphenylsulfonyl)-N'-(4-ethoxy-6-cyclopropyl-1,3,5-triazin-2-yl) urea.

* * * * *